United States Patent [19]

Smith

[11] 4,039,553
[45] Aug. 2, 1977

[54] CERTAIN 2(2'-HYDROXYPHENYL)BENZOTHIAZOLO DERIVATIVES

[75] Inventor: Richard F. Smith, Morristown, N.J.

[73] Assignee: GAF Corporation, New York, N.Y.

[21] Appl. No.: 656,988

[22] Filed: Feb. 10, 1976

Related U.S. Application Data

[60] Division of Ser. No. 444,988, Feb. 22, 1974, Pat. No. 3,972,875, which is a continuation of Ser. No. 818,386, April 22, 1969, abandoned, and Ser. No. 173,667, Aug. 20, 1971, abandoned.

[51] Int. Cl.² .......................................... C07D 277/66
[52] U.S. Cl. ......................... 260/304 R; 260/294.8 C; 260/256.5 R; 260/250 BN; 260/250 AH; 542/422
[58] Field of Search .................... 260/304 P, 294.8 C, 260/256.5 R, 250 BN, 250 AH, 240 G

[56] References Cited

U.S. PATENT DOCUMENTS

| | | | |
|---|---|---|---|
| 3,164,603 | 1/1965 | McCafferty | 260/304 P |
| 3,723,449 | 3/1973 | Wirth | 260/304 P |

Primary Examiner—R. J. Gallagher
Attorney, Agent, or Firm—W. C. Kehm; M. J. Maue

[57] ABSTRACT

Novel 2(2'-hydroxyaminophenyl)benzothiazoles and the Schiff Bases thereof having the formula:

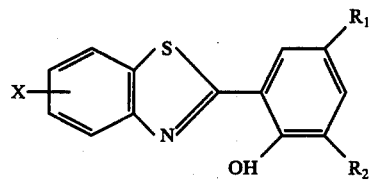

wherein X represents hydrogen, $SO_3H$, alkyl, aryl, cycloalkyl, or halogen; and wherein $R_1$ and $R_2$ represent X, amino or $N=CHR_3$ and one of the radicals $R_1$ and $R_2$ must be amino or $N=CHR_3$; $R_3$ represents alkyl, aryl, cycloalkyl, arylalkyl or nitrogen heterocyclic radicals having 4 or 5 carbon atoms.

6 Claims, No Drawings

CERTAIN 2(2-HYDROXYPHENYL)BENZOTHIAZOLO DERIVATIVES

This is a division of application of Ser. No. 444,988, filed Feb. 22, 1974, now U.S. Pat. No. 3,972,875, issued Aug. 3, 1976, which is a continuation of application Ser. No. 818,386 filed Apr. 22, 1969, now abandoned and Ser. No. 173,667, filed Aug. 20, 1971 also now abandoned.

The instant invention is directed to novel amino or imido derivative of 2(2-hydroxyphenyl) benzothiazoles. In particular, the instant invention is directed to novel 2(2'-hydroxyaminophenyl)benzothiazoles and the Schiff Bases thereof, such as 2(2'-hydroxyaldiminophenyl)benzothiazoles.

The novel compounds of the instant invention have the general formula:

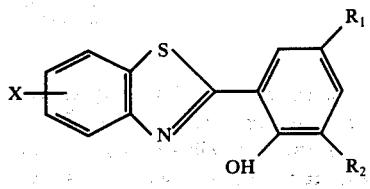

wherein X represents hydrogen, $SO_3H$, alkyl, aryl, cycloalkyl, nitrogen heterocyclic or halogen; and wherein $R_1$ and $R_2$ represent X, amino or $N\!=\!CHR_3$ and one of the radicals of $R_1$ and $R_2$ must be amino or $N\!=\!CHR_3$;

$R_3$ represents alkyl, aryl, cycloalkyl, arylalkyl, nitrogen heterocyclic radicals having 4 or 5 carbon atoms.

The instant invention is further directed to the preparation of fluorescent organic compounds such as the hydroxyaminophenylbenzothiazoles and the corresponding Schiff Bases which compounds fluoresce with a red hue. In the past, there have been few pure organic compounds which fluoresce with a red hue. Compounds presently employed which fluoresce red are the europium compounds, which compounds are conventionally employed in the colored television tubes. These compounds, however, have been found to be exceedingly expensive and extensive research has been concerned with finding a suitable and inexpensive substitute therefore.

Therefore, it is an object of the instant invention to provide new and novel benzothiazole compounds.

Another object of the instant invention is to provide benzothiazole compounds which are suitable as dyes which fluoresce with a red hue.

Yet another object of the invention is to provide novel chemical intermediates and products which are compounds which fluoresce in the red range.

A still further object of the instant invention is to provide novel organic compounds which fluoresce with a red hue which can be economically produced and which are suitable as color impregnators of television tubes.

These and other objects of the instant invention will become more evident from the following more detailed discussion thereof.

The novel compounds of the instant invention may be represented by the general formula:

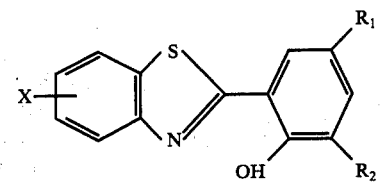

wherein X represents hydrogen, $SO_3H$, alkyl, aryl cycloalkyl, or halogen; and wherein $R_1$ and $R_2$ represent X, amino or $N\!=\!CHR_3$ and one of the radicals $R_1$ and $R_2$ must be amino or $N\!=\!CHR_3$;

$R_3$ represents alkyl, aryl, cycloalkyl, arylalkyl or nitrogen heterocyclic radicals having 4 or 5 carbon atoms.

Suitable alkyl radicals which may be employed for the substituents X, $R_1$, $R_2$ and $R_3$ include alkyl radicals having from 1 to 30 carbon atoms such as Methyl; Ethyl; Propyl; Isopropyl; Butyl; Tertiary Butyl; Pentyl; Hexyl; Methyl Hexyl; Heptyl; Octyl; Nonyl; Decyl; Undecyl; Dodecyl; Tridecyl; Tetradecyl; Pentadecyl; Hexadecyl; Heptadecyl; Octadecyl; Nonadecyl; Eicosyl; Docosyl; Tricosyl; Pentacosyl; Triacontyl;

and are preferably alkyl radicals having 1 to 6 carbon radicals.

Suitable cycloalkyl radicals which may be employed for X, $R_1$, $R_2$ and $R_3$ include but are not limited to:

Cyclopentyl; Cyclohexyl; Cycloheptyl; Cyclooctyl; Cyclononyl;

and are preferably cycloalkyl radicals having 5 or 6 membered rings. The phenyl alkyl substituent is a radical having 7 to 10 carbon atoms.

Suitable halogen radicals for X, $R_1$, $R_2$ and $R_3$ include Chloro; Bromo; Fluoro; Iodo;

and are preferably chloro and bromo.

Aryl radicals for X, $R_1$, $R_2$, and $R_3$ include phenyl or naphthyl whereas the phenyl ring can be further substituted with radicals including alkyl, of 1 to 4 carbon atoms, alkoxy of 1 to 9 carbon atoms, halogen as defined above carboxy, carboxyalkoxyacyl of 5 to 8 carbon atoms and acyl amino derivatives. Preferred aryl radicals of those above are phenyl and alkyl, alkoxy or halogen substituted phenyl radicals.

The hydroxy imino phenyl benzothiazole compounds of the present invention may be prepared by forming the hydroxy aminophenylbenzothiazole as a chemical intermediate and by reacting these intermediates with an aldehyde according to the standard Schiff reaction to form the corresponding Schiff Base. Specifically the hydroxyaminophenylbenzethiazole compounds of the instant invention may be prepared by condensing o-aminobenzenethiol with a particular salicylic acid in the presence of phosphorus acid chloride. Such a method of preparation is disclosed in co-pending application Ser. No. 690,376, now U.S. Pat. No 3,669,979 issued June 13, 1972. In this type of reaction, i.e. a phosphazo reaction of said U.S. Patent, the o-aminobenzenethiol is condensed with an appropriate salicylic acid in the presense of phosphorus trichloride. It is theorized that the aromatic amine first reacts with the phosphorus trichloride to form a phosphazo intermediate which intermediate subsequently reacts with the aromatic carboxylic acid to produce the anilide. This type of posphazo reaction is generally carried out in the presence of an organic solvent.

In general, the solvent that is employed is selected from aromatic hydrocarbon compounds and aromatic amines such as benzene, toluene, ortho-, meta- and para-xylene, dimethyl aniline and the like. The hydrocarbon solvents and in particular toluene and the aromatic amines such as dimethyl aniline are the preferred solvents for use in the preparation of the novel intermediate compounds of the instant invention. It has been found that the above two denoted solvents, result in a slightly higher yield of the desired amino intermediate compounds as compared to the other solvents which may be employed. The amount of solvent used in the preparation of th instant compounds is in no way critical and an excess thereof may be employed without interfering with the reaction or adversely affecting the yield or purity of the reaction product. The solvent that is employed in the system is readily removed from the reaction system subsequent to the completion of the reaction by conventional solvent removal processes.

The process employed in the preparation of the instant hydroxyaminophenylbenzothiazole intermediate compounds is generally carried out in two stages or steps. The first step in the reaction, i.e. the reaction of the o-aminobenzenethiol and phosphorus trichloride is exothermic and is generally carried out at a temperature from about 40° to 120° C and preferably at a temperature from about 50° C to about 90° C with external cooling. In this step the phosphazo intermediate is prepared by the reaction of phosphorus trichloride with the o-aminobenzenethiol. The second stage of the reaction between the phosphazo intermediate and the salicylic acid derivative is generally carried out at an elevated temperature from about 90° to about 180° C and preferably from about 105° to 120° C. The temperature employed is most preferably near the boiling point of the solvent so that reflux conditions can be utilized for recovering substantially pure product. It has been found that if one carries out both steps at an elevated temperature, an inferior product in low yield is produced. The process employed in connection with the instant invention can be carried out either by employing a single reaction vessel, initially kept at about 40° to 120° C with a subsequent raising of the temperature of reaction to a higher temperature up to 180° C or the process may be conducted in two separate reaction vessels. If the process is conducted in two separate reaction vessels, the product of the first reaction conducted at a lower temperature is completely removed and passed into the second vessel at a higher temperature in order to conduct the second step or stage of the reaction.

The reactants in the above process are employed in substantially stoichiometric amounts, athough it is also permissible to employ an excess of either of the reactants without imparing the purity, or yield of the reaction product.

The amount of phosphorus trichloride catalyst employed in the above reaction may vary greatly from about 0.5 moles to about 2 moles of phosphorus trichloride per mole of o-aminobenzenethiol or derivatives thereof. Preferably the phosphorus trichloride catalyst and the o-aminobenzenethiol or derivative are employed in substantially equal molar amounts. It is of course obvious that the lesser or greater amounts of catalyst can be employed where desired.

It has unexpectedly been found that the substitution in the 2' position of 2-(phenyl)benzothiazoles with a hydroxy substituent results in a marked enhancement of the fluorescent characteristics of the resultant compounds as compared with the 3' or 4' positions. It is believed that the intenseness of the fluorescence of these compounds as compared to those without 2' hydroxy substituent is due in part to an intramolecular hydrogen bonding which results in an increased copolanarity and therefore an enhanced fluorescence. This may be depicted by reference to the following equation, in which the intramolecular hydrogen bonding is illustrated.

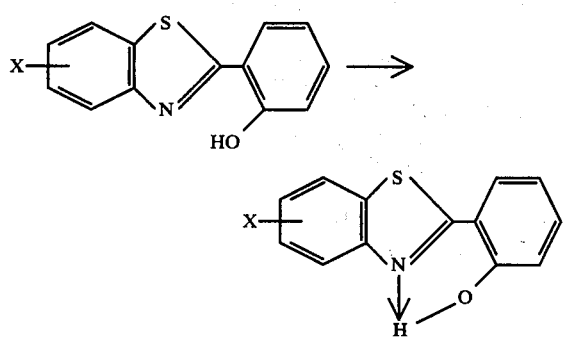

This effect is further established by a comparison of the absolute value of fluorescence of the numerous hydroxy substitutions possible on the phenyl ring of the benzothiazole. It has been found that, if one substitutes a hydroxy substituent in the 2' position, one obtains a brightness number of 41. However if, one substitutes the hydroxy substituent in either the 3' or 4' positions, one obtains a brightness number of only 6 and 11 respectively which variation in fluorescent values clearly indicates the unexpected effect of the compounds of the instant invention. Furthermore, a visual observation of hydroxyphenylbenzothiazole compounds indicates that the 2' substituted compound, i.e. 2(2'-hydroxyphenyl)-benzothiazole fluoresces with an intense green fluorescence, whereas the 2(3'-hydroxyphenyl)benzothiazole and 2(4'-hydroxyphenyl)benzothiazole fluoresces with a weak orange fluorescence and a barely perceptible orange fluorescence respectively. Surprisingly, in the 2(2'-hydroxyphenyl)benzothiazole compounds, the substitution of the amino groups or imido in the 3' or 5' positions results in a shifting of the fluorescence into the red area, that is to say, that when the amino groups are substituted in either the ortho or para positions relative to the hydroxy radical a compound which fluoresces with an intense red results.

In addition to the amino substituent in the 3' or 5' positions of the benzothiazole intermediate compounds of the instant invention, the corresponding Schiff Bases of these compounds have also been found to have these unique utilities. The corresponding Schiff Base products or aldimines may be readily prepared by the reaction of the corresponding primary amine, such as the amino intermediates prepared by the above method, with the desired aldehyde according to the following reaction scheme:

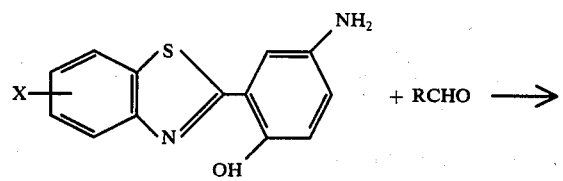

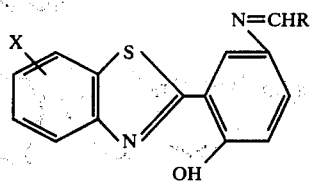

Process of this type are disclosed in Ann Sup., 3,343 (1864), JACS, 43,626 (1921) and is basically the standard Schiff reaction. The above Schiff reaction is carried out in the presence of an inert solvent such as an alcohol, methyl, ethyl ketone, acetone at a temperature between about 50° C and about 200° C, preferably under conditions of reflux at the pressure employed; atmospheric pressure being preferred.

The compounds of the instant invention are all water-insoluble. It is noted, however, that they can be solubilized by sulfonation as described in the co-pending application of H. B. Freyermuth, Ser. No. 690,791, filed Dec. 15, 1967 now U.S. Pat. No. 3,491,106, or by any other appropriate sulfonation process known in the art.

The instant invention will now be explained in more detail by reference to the following examples.

EXAMPLE I

2(2'-hydroxy-5'-aminophenyl)benzothiazole was prepared according to the following reaction process:

61 g. of 5-aminosalicylic acid was reacted with 50 g. of o-aminobenzenethiol in 500 ml. toluene. The reaction mixture was stirred and heated so as to dissolve the reactants and subsequently cooled to 60° C 17.5 ml. of phosphorus trichloride was then added and the reaction mixture was heated to reflux for 6 hours. At the end of this time the desired product precipitated and said product was filtered and air dried.

EXAMPLE II

2(2'-hydroxy-5'-benzlideneiminophenyl)benzothiazole was prepared according to the following process:

6 g. 2(2'-hydroxy-5'-aminophenyl)benzothiazole was prepared according to the method in Example I and was reacted with 3.4 g. benzaldehyde in 70 ml. of ethanol. The mixture was refluxed for 30 minutes, drowned in ice and the resultant solid product was filtered.

EXAMPLE III

2(2'-hydroxy-3'-aminophenyl)benzothiazole was prepared by reacting 3-aminosalicylic acid with o-aminobenzenethiol according to the process of Example I. At the end of 6 hours the desired product precipitated and said product was filtered and air-dried.

EXAMPLE IV

The corresponding Schiff Base of the product of the previous example was prepared according to the process of Example II by reacting said product with benzaldehyde in ethanol. The mixture was refluxed for thirty minutes, drowned in ice and the resultant product was filtered.

The following compounds are prepared under the temperature and pressure conditions of the above disclosure and in accordance with the procedure of the above examples by condensing a. an aminothiophenol having substituents corresponding to the substituents of the product in the benzothiazole moiety of the compound (e.g., such as those designated as Compound I in the above reference, U.S. Pat. No. 3,669,979) with b. aminosalicylic acid having substituents corresponding to the substituents of the product in phenol moiety of the compound to produce the corresponding 2(2-hydroxyaminophenyl) benzothiazole having the general formula:

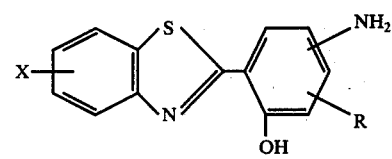

(1)

and/or reacting compound I having the desired substitution of the imido product with an aldehyde (e.g., acetaldehyde, ethylaldehyde, propionaldehyde, naphthaldehyde, xyloylaldehyde, halobenzaldehyde, butyraldehyde, tolualdehyde, dimethylbenzaldehyde, dimethoxybenzaldehyde, propylbenzaldehyde, pyridinecarboxaldehyde, pyrimidinecarboxaldehyde, carboxybenzaldehyde, formylbenzaldehyde, indolecarboxaldehyde) to provide the corresponding Schiff Base having the general formula:

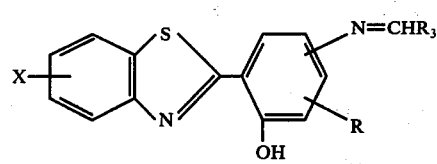

(2)

Specific products of this invention include the following:

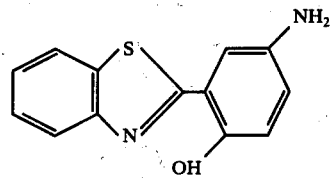

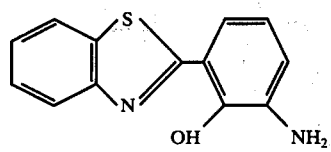

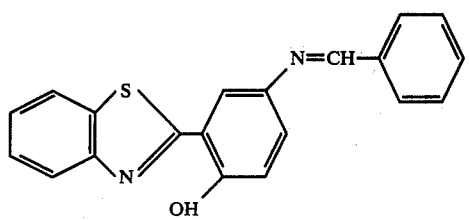

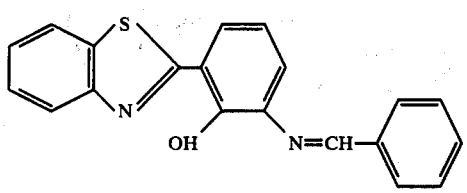

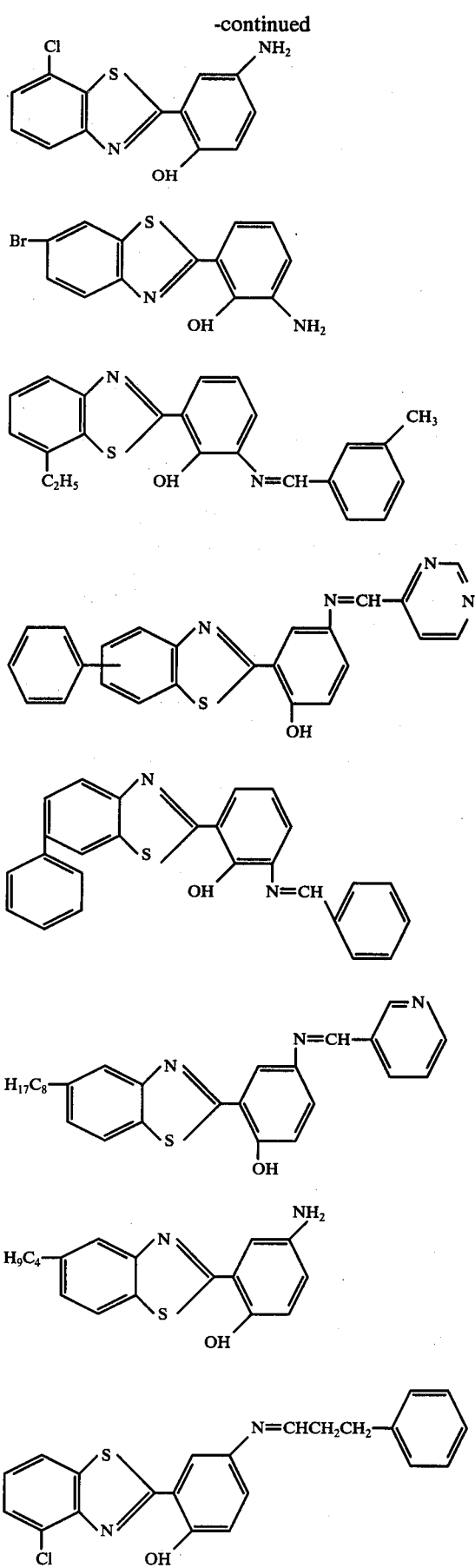

-continued

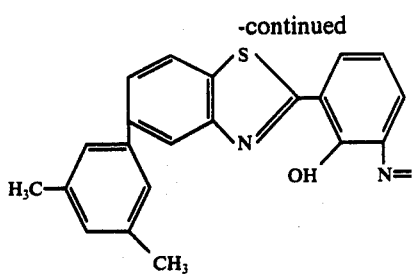

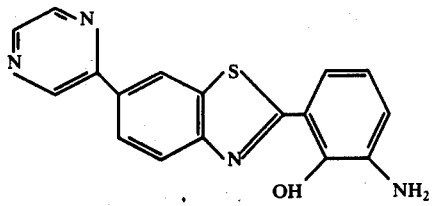

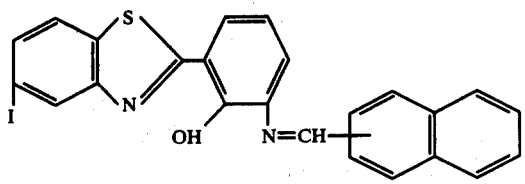

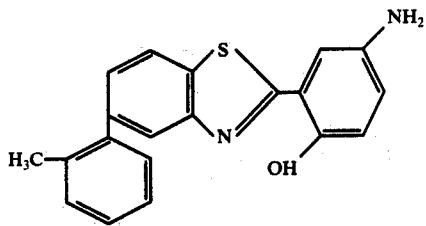

What is claimed is:

1. A red fluorescing 2-(2'-hydroxyphenyl)benzothiazole derivative having the formula:

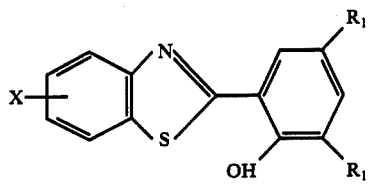

wherein $R_1$ or $R_2$ is $N=CHR_3$ and $R_3$ is selected from the group of alkyl having from 1 to 30 carbon atoms, alkoxy having from 1 to 4 carbon atoms or halo, and X and the other of $R_1$ and $R_2$ is hydrogen alkoxy of from 1 to 4 carbon atoms, $SO_3H$, halogen, alkyl as defined above, cycloalkyl of from 5 to 9 carbon atoms, nitrogen heterocyclic radical having 4 or 5 carbon atoms in an aromatically unsaturated 6-membered ring, phenyl, naphthyl or phenyl substituted by alkyl having from 1 to 4 carbon atoms, alkoxy having from 1 to 4 carbon atoms or halogen.

2. The compound of claim 1 wherein $R_1$ or $R_2$ is $N=CHR_3$ and $R_3$ is alkyl of from 1 to 6 carbon atoms and the other of $R_1$ and $R_2$ is hydrogen, cycloalkyl of from 5 to 9 carbon atoms or halogen and X is alkyl having 1 to 6 carbon atoms, cycloalkyl having 5 to 9 carbon atoms, halogen, phenyl, methylphenyl, methoxy, ethoxy, pyrazinyl, $-SO_3H$, or hydrogen.

3. The compound of claim 2 designated as 2(2'-hydroxy-3'-chloro-5'-propyliminephenyl)benzothiazole.

4. The compound of claim 2 designated as 2(2'-hydroxy-5'ethyliminephenyl)sulfo-benzothiazole.

5. The compound of claim 2 designated as 2(2'-hydroxy-3'-methylimine-5'-cyclohexyl phenyl)cyclohexyl-benzothiazole.

6. The compound of claim 2 designated as 2(2'-hydroxy-3'-methylimine-5'cyclohexylphenyl)benzothiazole.

* * * * *

UNITED STATES PATENT OFFICE
CERTIFICATE OF CORRECTION

PATENT NO. : 4,039,553
DATED : August 2, 1977
INVENTOR(S) : Richard F. Smith

It is certified that error appears in the above-identified patent and that said Letters Patent are hereby corrected as shown below:

On the Abstract page and in Column 1, please correct the title of the invention to read ---CERTAIN 2(2'-HYDROXYPHENYL) BENZOTHIAZOLE DERIVATIVES---.

Signed and Sealed this

Sixth Day of December 1977

[SEAL]

Attest:

RUTH C. MASON
Attesting Officer

LUTRELLE F. PARKER
Acting Commissioner of Patents and Trademarks